United States Patent [19]

Dürr

[11] 4,140,784
[45] Feb. 20, 1979

[54] NOVEL THIAZOLIDINES

[75] Inventor: Dieter Dürr, Bottmingen, Switzerland

[73] Assignee: Ciba-Geigy Corporation, Ardsley, N.Y.

[21] Appl. No.: 832,754

[22] Filed: Sep. 12, 1977

[30] Foreign Application Priority Data

Sep. 17, 1976 [CH] Switzerland ............ 11814/76
Aug. 9, 1977 [CH] Switzerland ............ 9734/77

[51] Int. Cl.² ............... A61K 31/425; C07D 277/18
[52] U.S. Cl. ........................ 424/270; 260/306.7 T
[58] Field of Search ............. 260/306.7 T; 424/270

[56] References Cited

U.S. PATENT DOCUMENTS 3,860,590  1/1975  Wollweber ............ 260/243 R

OTHER PUBLICATIONS

Burger, A. "Medicinal Chemistry", 2nd Ed., Interscience Publishers Inc., N.Y., 1963 (1064).

Morrison et al; Organic Chemistry, 3rd Edition, p. 1044 (1973).

Primary Examiner—Paul M. Coughlan, Jr.
Assistant Examiner—Lisa Jones
Attorney, Agent, or Firm—Harry Falber

[57] ABSTRACT

Thiazolidine-derivatives of the formula

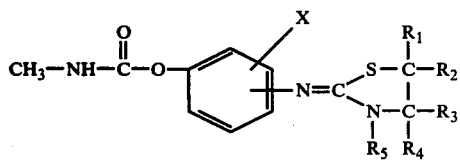

wherein
X is hydrogen, halogen or $C_1$–$C_4$-alkyl,
$R_1$, $R_3$ and $R_4$ are each hydrogen or $C_1$–$C_4$-alkyl,
$R_2$ is hydrogen, $C_1$–$C_4$-alkyl or $C_1$–$C_4$-alkoxy and
$R_5$ is $C_1$–$C_4$-alkyl, process for producing these thiazolidine-derivatives and their use in combating pests.

9 Claims, No Drawings

NOVEL THIAZOLIDINES

The present invention relates to thiazolidine derivatives and to salts thereof with inorganic and organic acids, to processes for producing them, and to their use in combating pests.

The thiazolidine derivatives have the formula

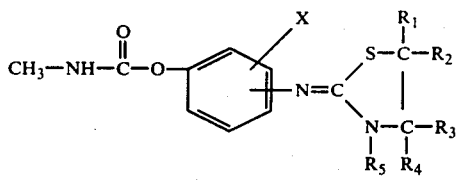

wherein
X is hydrogen, halogen or $C_1$-$C_4$-alkyl,
$R_1$, $R_3$ and $R_4$ are each hydrogen or $C_1$-$C_4$-alkyl,
$R_2$ is hydrogen, $C_1$-$C_4$-alkyl or $C_1$-$C_4$-alkoxy, and
$R_5$ is $C_1$-$C_4$-alkyl.

By halogen is meant fluorine, chlorine, bromine or iodine.

The alkyl and alkoxy groups denoted by $R_1$ to $R_5$ can be straight-chain or branched-chain. Examples of these groups are, inter alia: methyl, methoxy, ethyl, ethoxy, propyl or isopropyl or n-, i- or sec.-butyl.

Inorganic acids suitable for forming salts are, for example, HCl, $H_2SO_4$, HBr and $H_3PO_4$; and organic acids suitable for the purpose are, for example, saturated and unsaturated mono-, di- and tricarboxylic acids, such as formic acid, acetic acid, oxalic acid, phthalic acid and succinic acid.

Compounds of the formula I which are preferred by virtue of their action are those wherein X is hydrogen or methyl, $R_1$, $R_2$, $R_3$ and $R_4$ are each hydrogen, and $R_5$ is methyl or ethyl.

The compounds of the formula I can be produced for example by the following processes known per se:

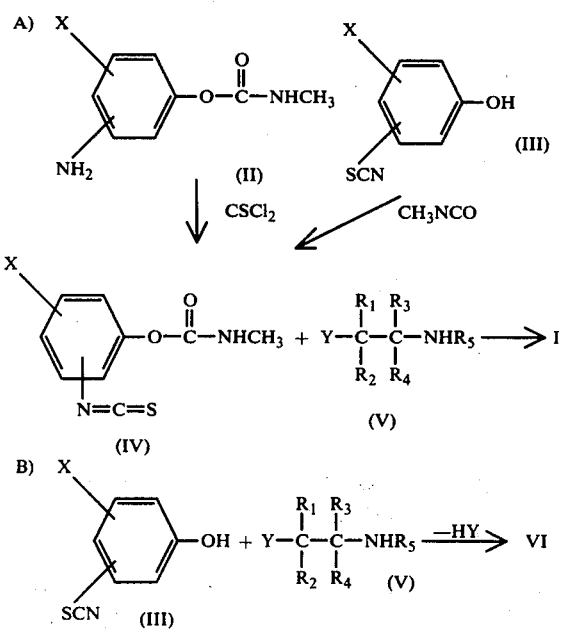

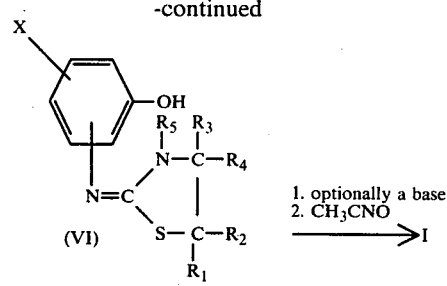

In the formulae II to VI, $R_1$ to $R_5$ and X have the meanings given for the formula I, and Y denotes halogen, preferably chlorine, bromine, hydroxyl or $C_1$-$C_4$-alkoxy. Suitable bases are, in particular, tertiary amines such as trialkylamines and pyridine; also hydroxides, oxides, and carbonates and bicarbonates of alkali metals and alkaline-earth metals.

The processes A and B are performed at a reaction temperature of $-20°$–$30\ 120°$ C., preferably at $20°$–$80°$ C., under normal pressure and in solvents or diluents.

Suitable solvents or diluents are, for example, ethers and ethereal compounds, such as diethyl ether, dipropyl ether, dioxane, dimethoxyethane or tetrahydrofuran; amides such as N,N-dialkylated carboxylic acid amides; aliphatic, aromatic as well as halogenated hydrocarbons, particularly benzene, toluene, xylenes, chloroform or chlorobenzene; nitriles such as acetonitrile; dimethylsulphoxide; and ketones such as acetone, methyl ethyl ketone; and water.

The starting materials of the formulae II, III and V are known or can be produced by processes analogous to known processes.

The active substances of the formula I are suitable for combating various animal and plant pests. The active substances thus possess nematocidal properties, and can be used for example for combating phytopathogenic nematodes. They are also suitable for combating viruses, bacteria and phytopathogenic fungi.

The compounds of the formula I are especially suitable for combating insects, and phytopathogenic mites and ticks, for example of the orders: Lepidoptera, Coleoptera, Homoptera, Heteroptera, Diptera, Acarina, Thysanoptera, Orthoptera, Anoplura, Siphonoptera, Mallophaga, Thyssanura, Isoptera, Psocoptera and Hymenoptera.

In particular, the compounds of the formula I are suitable for combating insects that damage plants, especially insects that damage plants by eating, in crops of ornamental plants and useful plants, particularly in cotton crops (e.g. against *Spodoptera littoralis* and *Heliothis virescens*) and in crops of vegetables (e.g. against *Leptinotarsa decemlineata* and *Myzus persicae*). The active substances of the formula I also have a very favourable action against flies, such as *Musca domestica*, and against mosquito larvae.

The acaricidal and insecticidal action can be substantially broadened and adapted to suit given circumstances by the addition of other insecticides and/or acaricides. Suitable additives are, for example, organic phosphorus compounds; nitrophenols and derivatives thereof; formamidines; ureas; other pyrethrin-like compounds; as well as carbamates and chlorinated hydrocarbons.

Compounds of the formula I are combined particularly advantageously with substances which have an intensifying effect. Examples of such compounds are, inter alia: piperonyl butoxide propynyl ethers, propynyl oximes, propynyl carbamates and propynyl phosphonates, 2-(3,4-methylenedioxyphenoxy)-3,6,9-trioxaundecane and S,S,S-tributylphosphorotrithioates.

The compounds of the formula I can be used on their own or together with suitable carriers and/or additives. Suitable carriers and additives may be solid or liquid, and they correspond to the substances common in formulation practice, such as natural or regenerated substances, solvents, dispersing agents, wetting agents, adhesives, thickeners, binders and/or fertilisers. For application, the compounds of the formula I can be processed into the form of dusts, emulsion concentrates, granulates, dispersions, sprays or solutions, the formulation of these preparations being effected in a manner commonly known in the art. Also to be mentioned are cattle dips and spray races, in which aqueous preparations are used.

The compositions according to the invention are produced in a manner known per se by the intimate mixing and/or grinding of active substances of the formula I with suitable carriers, optionally with the addition of dispersing agents or solvents which are inert to the active substances. The active substances can be obtained and used in the following forms:

solid preparations:
 dusts, scattering agents or granulates (coated granulates, impregnated granulates and homogeneous granulates);

liquid preparations:
 (a) water-dispersible concentrates of active substance: wettable powders, pastes or emulsions;
 (b) solutions.

The content of active substance in the compositions described is between 0.1 and 95%. The active substances of the formula I can be formulated for example as follows:

Dusts

The following substances are used to produce (a) a 5% dust and (b) a 2% dust:

(a)
 5 parts of active substance,
 95 parts of talcum;

(b)
 2 parts of active substance,
 1 part of highly dispersed silicic acid,
 97 parts of talcum.

The active substances are mixed and ground with the carriers.

Granulate

The following substances are used to produce a 5% granulate:
 5 parts of active substance,
 0.25 part of epichlorohydrin,
 0.25 part of cetyl polyglycol ether,
 3.50 parts of polyethylene glycol,
 91 parts of kaolin (particle size 0.3–0.8 mm).

The active substance is mixed with the epichlorohydrin and dissolved with 6 parts of acetone; the polyethylene glycol and cetyl polyglycol ether are then added. The solution obtained is sprayed onto kaolin, and the acetone is evaporated off.

Wettable powders

The following constituents are used to produce (a) a 40%, (b) and (c) a 25%, and (d) a 10% wettable powder:

(a)
 40 parts of active substance,
 5 parts of sodium lignin sulphonate,
 1 part of sodium dibutyl-naphthalene sulphonate,
 54 parts of silicic acid;

(b)
 25 parts of active substance,
 4.5 parts of calcium lignin sulphonate,
 1.9 parts of Champagne chalk/hydroxyethyl cellulose mixture (1:1),
 1.5 parts of sodium dibutyl naphthalene sulphonate,
 19.5 parts of silicic acid,
 19.5 parts of Champagne chalk,
 28.1 parts of kaolin;

(c)
 25 parts of active substance,
 2.5 parts of isooctylphenoxy-polyoxyethylene-ethanol,
 1.7 parts of Champagne chalk/hydroxyethyl cellulose mixture (1:1),
 8.3 parts of sodium aluminium silicate,
 16.5 parts of kieselguhr,
 46 parts of kaolin;

(d)
 10 parts of active substance,
 3 parts of a mixture of the sodium salts of saturated fatty alcohol sulphates,
 5 parts of naphthalenesulphonic acid/formaldehyde condensate,
 82 parts of kaolin.

The active substances are intimately mixed in suitable mixers with the additives, and the mixture is then ground in the appropriate mills and rollers. There are obtained wettable powders which can be diluted with water to give suspensions of the desired concentration.

Emulsifiable concentrate

The following substances are used to produce (a) a 10%, (b) a 25%, and (c) a 50% emulsifiable concentrate:

(a)
 10 parts of active substance,
 3.4 parts of epoxidised vegetable oil,
 3.4 parts of a combination emulsifier consisting of fatty alcohol polyglycol ether and alkylarylsulphonate calcium salt,
 40 parts of dimethylformamide,
 43.2 parts of xylene;

(b)
 25 parts of active substance,
 2.5 parts of epoxidised vegetable oil,
 10 parts of alkylarylsulphonate/fatty alcohol polyglycol ether mixture,
 5 parts of dimethylformamide,
 57.5 parts of xylene;

(c)
 50 parts of active substance,
 4.2 parts of tributylphenol-polyglycol ether,
 5.8 parts of calcium-dodecylbenzenesulphonate,
 20 parts of cyclohexanone,
 20 parts of xylene.

Emulsions of the desired concentration can be prepared from these concentrates by dilution with water.

Spray

The following constituents are used to produce (a) a 5% spray and (b) a 95% spray:

(a)
- 5 parts of active substance,
- 1 part of epichlorohydrin,
- 94 parts of ligroin (boiling limits 160°–190° C.), (b)
- 95 parts of active substance,
- 5 parts of epichlorohydrin.

The invention is further illustrated by the following Examples.

EXAMPLE 1

Production of 2-(4-N-methylcarbamoyloxy-phenylimino)-3-methyl-thiazolidine

A 1) 16 g of 2-methylamino-ethanol is added to 30 g of 4-hydroxyphenyl mustard oil in 100 ml of toluene. After 1 hour, there is added 100 ml of concentrated hydrochloric acid, and the mixture is refluxed with vigorous stirring. After a further hour, the reaction mixture is cooled, the aqueous phase is separated, and rendered alkaline with sodium carbonate solution. A white precipitate is formed; the precipitate is collected on a suction filter, washed with water and subsequently dried to thus obtain the compound of the formula

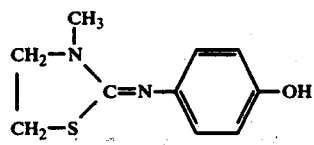

having a melting point of 225°–227° C.

A 2) 28 g of (2-(4-hydroxyphenylimino)-3-methyl-thiazolidine is dissolved in 150 ml of dioxane and 50 ml of dimethylformamide, and 10 ml of methylisocyanate is added. After 72 hours, the solution is concentrated by evaporation, and the residue is extracted by stirring with ice water, filtered off with suction and dried. Recrystallisation from ethyl acetate/hexane yields the compound of the formula

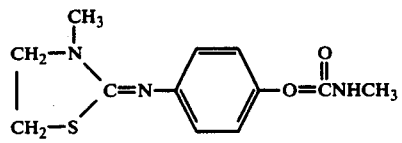

having a melting point of 95°–97° C.

The following compounds are produced in an analogous manner:

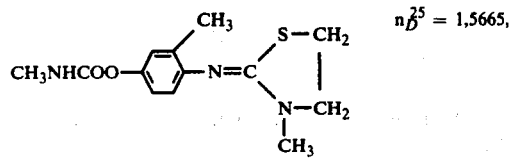
$n_D^{25} = 1.5665$,

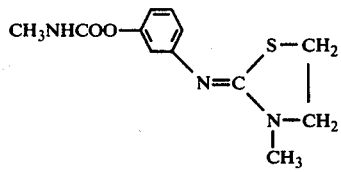
m.p. 97–99° C.,

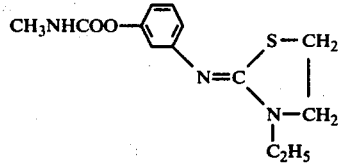
m.p. 95–97° C.,

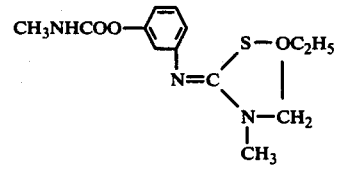
m.p. 87° C.

EXAMPLE 2

(A) Insecticidal stomach-poison action

Cotton plants were sprayed with a 0.05% aqueous emulsion of the active substance (obtained from a 10% emulsifiable concentrate).

After drying of the coating, larvae of *Spodoptera littoralis* in the $L_3$-stage and of *Heliothis virescens* in the $L_3$-stage were placed onto the cotton plants. The test was carried out at 24° C. with 60% relative humidity.

Compounds according to Example 1 exhibited in the above test a good insecticidal stomach-poison action against larvae of *Spodoptera littoralis* and *Heliothis virescens*.

(B) Systemic insecticidal action

In order to determine the systemic action, rooted bean plants (*Vicia faba*) were placed into a 0.01% aqueous solution of the active substance (obtained from a 10% emulsifiable concentrate). After 24 hours, bean aphids (*Aphis fabae*) were placed onto the parts of the plants that had been above the soil. By means of a special device, the bean aphids were protected from the effects of contact and of gas. The test was carried out at 24° C. with 70% relative humidity.

Compounds according to Example 1 exhibited in the above test a systemic insecticidal action against *Aphis fabae*.

EXAMPLE 3

Action against *Chilo suppressalis*

Rice plants of the variety Caloro were planted six plants per pot in plastic pots having an upper diameter of 17 cm, and grown to a height of about 60 cm. Infestation with *Chilo suppressalis* larvae ($L_1$; 3–4 mm long) was carried out 2 days after application of the active substance in granular form (amount applied = 8 kg of active substance per hectare) to the paddy water. An evaluation of the insecticidal action was made 10 days after application of the granules.

Compounds according to Example 1 exhibited in the above test a good action against *Chilo suppressalis*.

EXAMPLE 4

Acaricidal action

*Phaseolus vulgaris* plants were infested, 12 hours before the test for acaricidal action, with an infested piece of leaf from a mass culture of *Tetranychus urticae*. The transferred mobile stages were sprayed with the emulsified test preparations from a chromatography-sprayer in a manner ensuring no overflow of the spray liquor. An assessment was made after 2 to 7 days, by examination under a binocular microscope, of the living and of the dead larvae, adults and eggs, and the results were expressed as percentages. The treated plants were kept during the "holding time" in greenhouse compartments at 25° C.

Compounds according to Example 1 exhibited in the above test a good action against adults, larvae and eggs of *Tetranychus urticae*.

EXAMPLE 5

Action against soil nematodes

In order to test their action against soil nematodes, the active substances were added to soil infested with root-gall nematodes (*Meloidogyne arenaria*), and intimately mixed with the soil. In one test series, tomato seedlings were planted immediately after preparation of the soil in this manner, and in the other test series tomatoes were sown after a waiting time of 8 days. As assessment of the nematocidal action was made by counting the galls present on the roots 28 days after planting and sowing, respectively.

Active substances according to Example 1 exhibited in this test a good action against *Meloidogyne arenaria*.

EXAMPLE 6

Action against ticks (A) *Rhipicephalus bursa*

For each concentration, 5 adult ticks and 50 tick larvae, respectively, were counted into a small glass test tube, and immersed for 1 and 2 minutes in 2 ml of an aqueous emulsion from a dilution series of 100, 10, 1 and 0.1 ppm of test substance. The tubes were then sealed with a standardised cotton plug, and inverted so that the active-substance emulsion could be absorbed by the cotton wool.

The evaluation in the case of the adults was made after 2 weeks and in the case of the larvae after 2 days. There were two repeats for each test.

(B) *Boophilus microplus* (larvae)

With a dilution series analogous to that of Test A, tests were carried out with 20 sensitive larvae and OP-resistant larvae, respectively (resistance is with respect to diazinon compatibility).

Compounds according to Example 1 were effective in these tests against adults and larvae of *Rhipicephalus bursa* and against sensitive and OP-resistant larvae, respectively, of *Boophilus microplus*.

I claim:

1. A thiazolidine compound of the formula

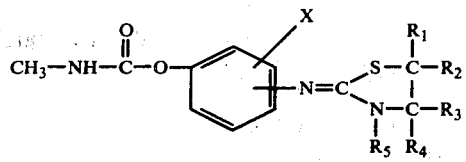

wherein
X is hydrogen, halogen or $C_1$-$C_4$-alkyl,
$R_1$, $R_3$ and $R_4$ are each hydrogen or $C_1$-$C_4$-alkyl,
$R_2$ is hydrogen, $C_1$-$C_4$-alkyl or $C_1$-$C_4$-alkoxy, and
$R_5$ is $C_1$-$C_4$-alkyl, and salts thereof with inorganic acids selected from the group consisting of hydrochloric, sulfuric, hydrobromic and phosphoric acids, and with organic acids selected from the group consisting of formic, acetic, oxalic, phthalic and succinic acids.

2. A thiazolidine derivative according to claim 1, wherein X is hydrogen or methyl; $R_1$, $R_2$, $R_3$ and $R_4$ are each hydrogen; and $R_5$ is methyl or ethyl.

3. A thiazolidine compound according to claim 2, of the formula

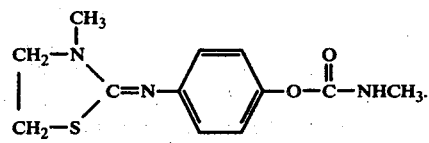

4. A thiazolidine compound according to claim 2, of the formula

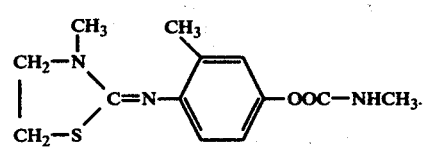

5. A thiazolidine compound according to claim 2, of the formula

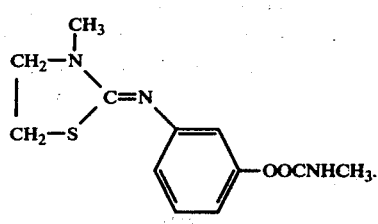

6. A thiazolidine compound according to claim 2, of the formula

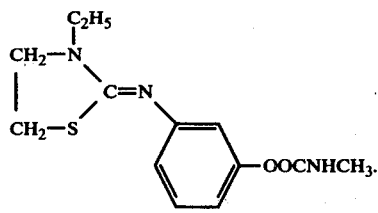

7. A thiazolidine compound according to claim 1, of the formula

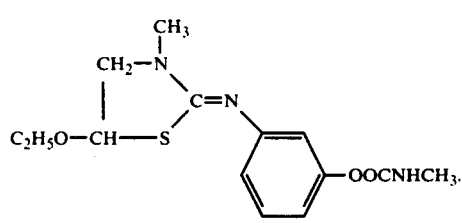
8. An insectidal and acaricidal composition comprising an insecticidally or acaricidally effective amount of a compound of claim 1, together with a suitable carrier therefor.
9. A method of combatting insects and acarids which comprises applying to the locus thereof an insecticidally or acaricidally effective amount of a compound of claim 1.
* * * * *